United States Patent
Zou

(10) Patent No.: US 9,397,301 B2
(45) Date of Patent: Jul. 19, 2016

(54) SULFONE GROUP-CONTAINING COMPOUND, AN ORGANIC LIGHT EMITTING DIODE (OLED) DEVICE HAVING THE SAME, AND A METHOD OF FABRICATING THE OLED DEVICE

(71) Applicant: Shenzhen China Star Optoelectronics Technology Co., Ltd., Shenzhen, Guangdong (CN)

(72) Inventor: Qinghua Zou, Shenzhen (CN)

(73) Assignee: Shenzhen China Star Optoelectronics Technology Co., Ltd, Shenzhen, Guangdong (CN)

( * ) Notice: Subject to any disclaimer, the term of this patent is extended or adjusted under 35 U.S.C. 154(b) by 511 days.

(21) Appl. No.: 13/985,938

(22) PCT Filed: Jun. 25, 2013

(86) PCT No.: PCT/CN2013/077939
§ 371 (c)(1),
(2) Date: Aug. 16, 2013

(87) PCT Pub. No.: WO2014/180037
PCT Pub. Date: Nov. 13, 2014

(65) Prior Publication Data
US 2015/0357584 A1 Dec. 10, 2015

(30) Foreign Application Priority Data
May 6, 2013 (CN) .......................... 2013 1 0163001

(51) Int. Cl.
*H01L 51/00* (2006.01)
*C07D 409/14* (2006.01)
*C07F 7/08* (2006.01)
*C07D 333/76* (2006.01)
(Continued)

(52) U.S. Cl.
CPC .......... *H01L 51/0074* (2013.01); *C07D 333/76* (2013.01); *C07D 409/14* (2013.01);
(Continued)

(58) Field of Classification Search
CPC .. C07D 333/76; C07D 409/14; C07F 7/0812; H01L 51/001; H01L 51/0061; H01L 51/0067; H01L 51/0074; H01L 51/0094; H01L 51/5012; H01L 51/5072; H01L 51/56; C09K 11/06

See application file for complete search history.

(56) References Cited

U.S. PATENT DOCUMENTS

2014/0209867 A1* 7/2014 Zou .................... H01L 51/0074
257/40

FOREIGN PATENT DOCUMENTS

CN 1749314 A 10/2006
CN 101331626 B 12/2008
(Continued)

Primary Examiner — Dawn Garrett
(74) Attorney, Agent, or Firm — Andrew C. Cheng

(57) ABSTRACT

The present invention provides a sulfone group-containing compound, an organic light emitting diode (OLED) device using the sulfone group-containing compound, and a method of fabricating the OLED device. The sulfone group-containing compound has formula as

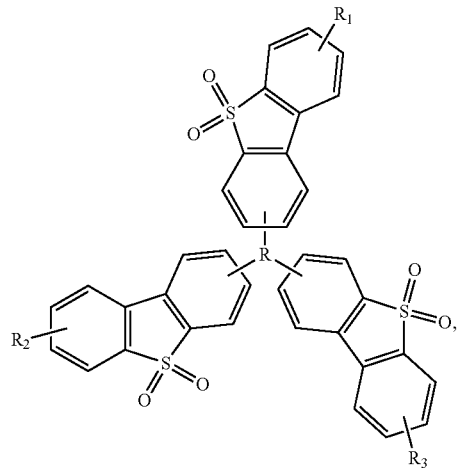

wherein the bridging unit R is capable of connecting to three or more than three fluorene sulfur oxide units; and the unit $R_1$, $R_2$ and $R_3$ respectively connected to the fluorene sulfur oxide units are selected from alkyl chains, aromatic groups or heterocyclic groups. According to the present invention, the sulfone group-containing compound connects to three or more than three fluorene sulfur oxide units with a bridging unit to form a novel star-shaped molecular structure. The sulfone groups-containing compound combines electron affinity and transport properties of the fluorene sulfur oxide units and spatial characteristics of the star-shaped molecular structure, so that efficiency and lifetime of an OLED device using the same can be enhanced.

10 Claims, 6 Drawing Sheets

(51) Int. Cl.
*C09K 11/06* (2006.01)
*H01L 51/56* (2006.01)
*H01L 51/50* (2006.01)

(52) U.S. Cl.
CPC .............. *C07F 7/0812* (2013.01); *C09K 11/06* (2013.01); *H01L 51/0061* (2013.01); *H01L 51/0067* (2013.01); *H01L 51/0094* (2013.01); *H01L 51/001* (2013.01); *H01L 51/5012* (2013.01); *H01L 51/5072* (2013.01); *H01L 51/56* (2013.01)

(56) References Cited

FOREIGN PATENT DOCUMENTS

| | | |
|---|---|---|
| CN | 101461074 A | 6/2009 |
| CN | 101971384 A | 2/2011 |
| CN | 101993410 A | 3/2011 |
| JP | 2007126403 A1 | 5/2007 |
| WO | WO2012033063 A1 | 3/2012 |
| WO | WO2012141273 A1 | 10/2012 |

* cited by examiner

SULFONE GROUP-CONTAINING COMPOUND, AN ORGANIC LIGHT EMITTING DIODE (OLED) DEVICE HAVING THE SAME, AND A METHOD OF FABRICATING THE OLED DEVICE

FIELD OF THE INVENTION

The present invention relates to a technique of organic light emitting, more particularly to a sulfone group-containing compound, an organic light emitting diode (OLED) device using the same, and a method of fabricating the OLED device.

BACKGROUND OF THE INVENTION

An organic light emitting diode (OLED) device is a self-luminescence device, and has ascendancies such as low operating voltage, wide viewing angle, fast response and temperature adaptability, so that the OLED device is a new generation of display technique. Recently, the OLED panel has been fabricated with a commercial yield by few manufacturers, and some companies also enter R&D and commercial yield phases of the OLED device.

The luminescence principle of the OLED device is that holes and electrons are respectively injected from anode and cathode; then the holes pass through hole injection and transport layer electron injection layer, the electrons pass through electron injection and transport layer; then combination of the holes and the electrons provides energy to form excitons in light emitting layer; and the excitons radiate luminescence due to attenuation from excited state to bound state of exciting electrons of the excitons.

A key point of enhancing efficiency and lifetime of the OLED device is equilibrium between a hole-concentration current and an electron-concentration current in a light emitting layer of OLED device. However, an electron mobility of a conventional electron-transporting material is about $10^{-5}$ $cm^2v^{-1}s^{-1}$-$10^{-6}$ $cm^2v^{-1}s^{-1}$, a hole mobility of a conventional hole-transporting material is about $10^{-2}$ $cm^2v^{-1}s^{-1}$-$10^{-3}$ $cm^2v^{-1}s^{-1}$, and the hole mobility of the conventional hole-transporting material is about 1000 times of the electron mobility of the conventional electron-transporting material, so that a difference between the hole mobility and the electron mobility thereof causes un-equilibrium of the hole-concentration current and the electron-concentration current in the light emitting layer of OLED device. The un-equilibrium between the hole-concentration current and the electron-concentration current allows the combination zone of the holes and electrons be formed nearby cathode, and produces excess hole-concentration current to quench the excitons formed in the light emitting layer, so as to decrease the efficiency and lifetime of the OLED device. For the aspect of enhancing the efficiency and lifetime of the OLED device, an electron-transporting material has need to meet demands of higher electron mobility, higher electron affinity, and stronger electron-accepting and electron-transporting ability.

Another key point of enhancing efficiency and lifetime of OLED device is that the combination zone of the holes and the electrons can be set in the entire light emitting layer, accordingly, a host material of radiating phosphorescence for electroluminescence devices shall be a dipole material having both high hole and electron mobility. Most of currently available materials of radiating phosphorescence are not a dipole material (i.e. have not both high hole and electron mobility), a great difference between the hole and the electron mobility thereof allows the combination zone of the holes and electrons be formed nearby one side of the OLED device (e.g. cathode), but not in the entire light emitting layer, moreover, the excess hole-concentration or electron-concentration current quenches the excitons formed in the light emitting layer, so as to seriously decrease the efficiency and lifetime of the OLED device.

Fluorene sulfur oxide is a novel electron-lacked (i.e. hole type) compound and also a derivative of fluorene, which has a substituent of sulfone group (—$SO_2$) at C-9. The sulfone group is an electron-withdrawing group, and has higher electron affinity and an energy band gap of approximately 2.8 eV; therefore, the fluorene sulfur oxide can easily conduct electrons for injection and transport. S atom in the sulfone group is at the highest valence state, so as the sulfone group can be a stronger antioxidant, thus the fluorene sulfur oxide has a strong thermal stability. These advantages of the fluorene sulfur oxide allow the fluorene sulfur oxide be a useful material for transporting electrons in the OLED device.

Due to star-shaped molecule structure, a compound of a star-shaped molecule structure has characteristics such as great molecular weight, large steric, high glass-transition temperature, poor crystallinity and easily forming a stable amorphous film. Currently, publicly used compounds have a star-shaped molecule structure, formed by a bridging unit, such as following compounds:

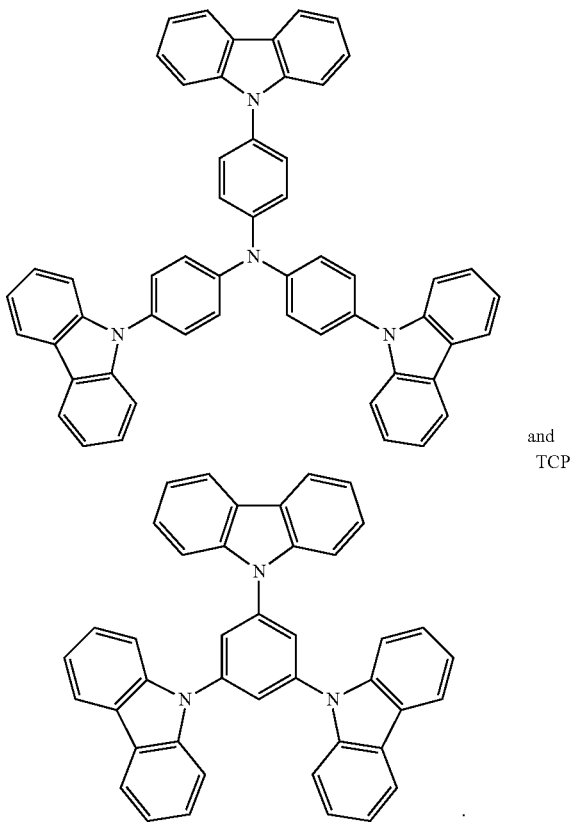

TCTA and
TCP

SUMMARY OF THE INVENTION

In accordance with an aspect, the present invention provides a sulfone group-containing compound. The sulfone group-containing compound has three or more than three fluorene sulfur oxide units connected with a bridging unit to form a novel star-shaped molecular structure. The sulfone groups-containing compound combines electron affinity and transport properties of the fluorene sulfur oxide units and spatial characteristics of the star-shaped molecular structure.

In accordance with another aspect, the present invention provides an OLED device using the sulfone group-containing compound. At least a light emitting layer or electron transport layer in the OLED device includes the sulfone group-containing compound according to the present invention, the sulfone group-containing compound increases electron-injecting and electron-transporting abilities of the OLED device, and allows combination zone of hole-concentration current and electron-concentration current be formed in the entire light emitting layer, and it can be formed as a stable amorphous film. Therefore, efficiency and lifetime of the OLED device can be enhanced with the sulfone group-containing compound.

In accordance with another aspect, the present invention provides a method of fabricating an OLED using the sulfone group-containing compound, the method according to the present invention applies the sulfone group-containing compound to a light emitting layer or an electron transport layer in the OLED device, the sulfone group-containing compound increases electron-injecting and electron-transporting abilities of the OLED device, and allows combination zone of hole-concentration current and electron-concentration current be formed in the entire light emitting layer, and it can be formed as a stable amorphous film. Therefore, efficiency and lifetime of the OLED device can be enhanced with the sulfone group-containing compound.

For the above aspects, the sulfone group-containing compound according to the present invention has a formula as

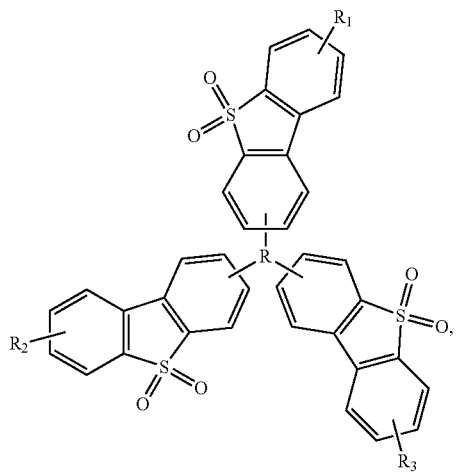

wherein the bridging unit R is capable of connecting to three or more than three fluorene sulfur oxide units; and the unit $R_1$, $R_2$ and $R_3$ respectively connected to the fluorene sulfur oxide units are selected from alkyl chains, aromatic groups or heterocyclic groups.

In a preferred embodiment, the bridging unit R capable of connecting to three or more than three fluorene sulfur oxide units is selected from

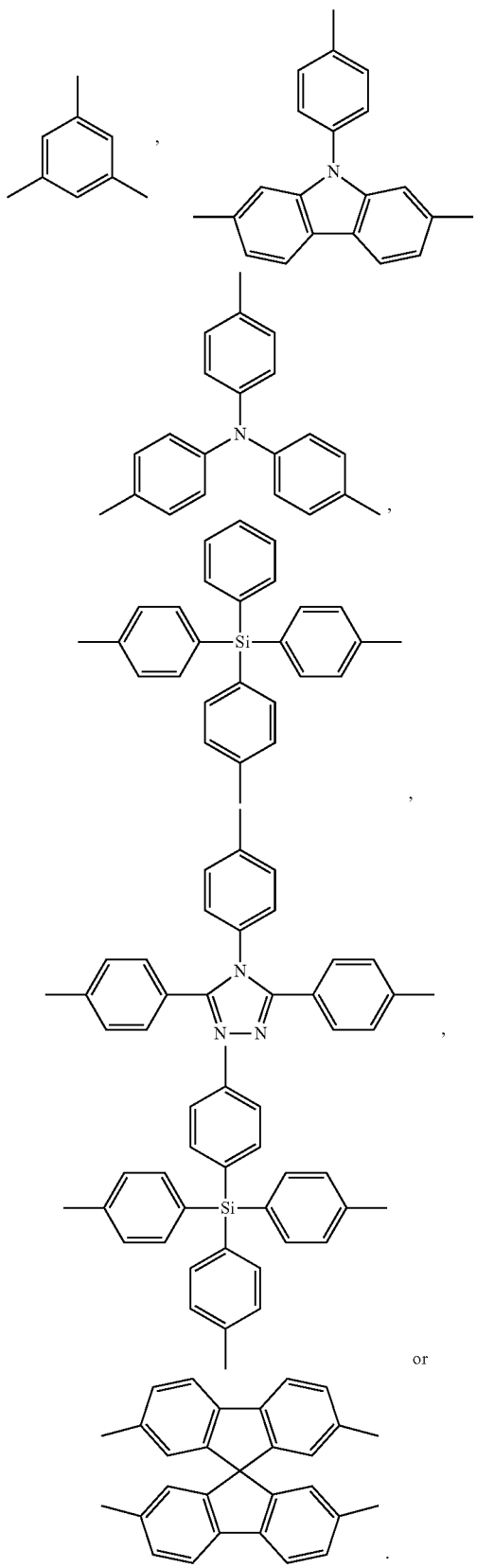

In a preferred embodiment, the alkyl chains are selected from a branched alkyl chain or straight alkyl chains.

In a preferred embodiment, the branched alkyl chain is $$-\underset{\underset{CH_3}{|}}{\overset{\overset{CH_3}{|}}{C}}-CH_3,$$

and the straight alkyl chains have formula as $$-(CH_2)_n-CH_3,$$

wherein the integer n is in 1-8.

In a preferred embodiment, the aromatic groups are selected from

[phenyl], [4-methylphenyl], [3-methylphenyl], [2-methylnaphthyl], or [1-methylnaphthyl].

In a preferred embodiment, the heterocyclic groups are selected from

[3-pyridyl], [4-methylpyridyl], [2-methylpyridyl], [8-methylquinolinyl], [7-methylquinolinyl] or [6-methylquinolinyl].

In accordance with the present invention, the OLED device using the sulfone group-containing compound includes a transparent substrate, an anode, a hole transport layer, a light emitting layer, an electron transport layer and a cathode. The anode is disposed above the transparent substrate. The hole transport layer is disposed above the anode. The light emitting layer is disposed above the hole transport layer. The electron transport layer is disposed above the light emitting layer. The cathode is disposed above the electron transport layer. At least the electron transport layer or the light emitting layer includes a sulfone group-containing compound having formula as

[chemical structure with three fluorene sulfur oxide units connected by bridging unit R, with substituents $R_1$, $R_2$, and $R_3$]

wherein the bridging unit R is capable of connecting to three or more than three fluorene sulfur oxide units; and the unit $R_1$, $R_2$ and $R_3$ respectively connected to the fluorene sulfur oxide units are selected from alkyl chains, aromatic groups or heterocyclic groups.

In a preferred embodiment, the sulfone group-containing compound is a single body material of the light emitting layer or one component of plural body materials contained in the light emitting layer, whereas the sulfone group-containing compound is one component of plural body materials contained in the light emitting layer, a weight ratio of the sulfone group-containing compound to the light emitting layer is in 1%~99%.

In a preferred embodiment, the sulfone group-containing compound is a single body material of the electron transport layer or one component of plural body materials contained in the electron transport layer, whereas the sulfone group-containing compound is one component of plural body materials contained in the electron transport layer, a weight ratio of the sulfone group-containing compound to the electron transport layer is in 1%~99%.

In accordance with the present invention, a method of fabricating the OLED device using the sulfone group-containing compound includes steps as follows:

Step 1, providing a transparent substrate;
Step 2, forming an anode above the transparent substrate;
Step 3, forming one or more than one hole transport layer above the anode;
Step 4, forming one or more than one light emitting layer above the hole transport layer;
Step 5, forming one or more than one electron transport layer above the light emitting layer; and
Step 6, forming a cathode above the electron transport layer, wherein at least one of the light emitting layer or the electron transport layer includes the sulfone group-containing compound according to the present invention.

In a preferred embodiment, Step 4 in the method of fabricating the OLED device using the sulfone group-containing compound includes the sulfone group-containing compound is formed above the hole transport layer with a vacuum evaporation deposition, the sulfone group-containing compound is a single body material of the light emitting layer or one component of plural body materials contained in the light emitting layer, whereas the sulfone group-containing compound is one of plural components contained in the light emitting layer, a weight ratio of the sulfone group-containing compound to the light emitting layer is in 1%~99%.

In a preferred embodiment, Step 5 in the method of fabricating the OLED device using the sulfone group-containing compound includes the sulfone group-containing compound is formed above the light emitting layer with a vacuum evaporation deposition, and the sulfone group-containing compound is a single body material of the light emitting layer or one component of plural body materials contained in the light emitting layer, whereas the sulfone group-containing compound is one component of plural body materials contained in the light emitting layer, a weight ratio of the sulfone group-containing compound to the light emitting layer is in 1%~99%.

According to the present invention, the sulfone group-containing compound connects to three or more than three fluorene sulfur oxide units with a bridging unit to form a novel star-shaped molecular structure. The sulfone groups-containing compound combines electron affinity and transport properties of the fluorene sulfur oxide units and spatial characteristics of the star-shaped molecular structure, so that efficiency and lifetime of the OLED device can be enhanced with the sulfone group-containing compound.

BRIEF DESCRIPTION OF THE DRAWINGS

The above objects and advantages of the present invention will become more readily apparent to those ordinarily skilled in the art after reviewing the following detailed description and accompanying drawings, in which.

DETAILED DESCRIPTION OF PREFERRED EMBODIMENTS

Figure 1:
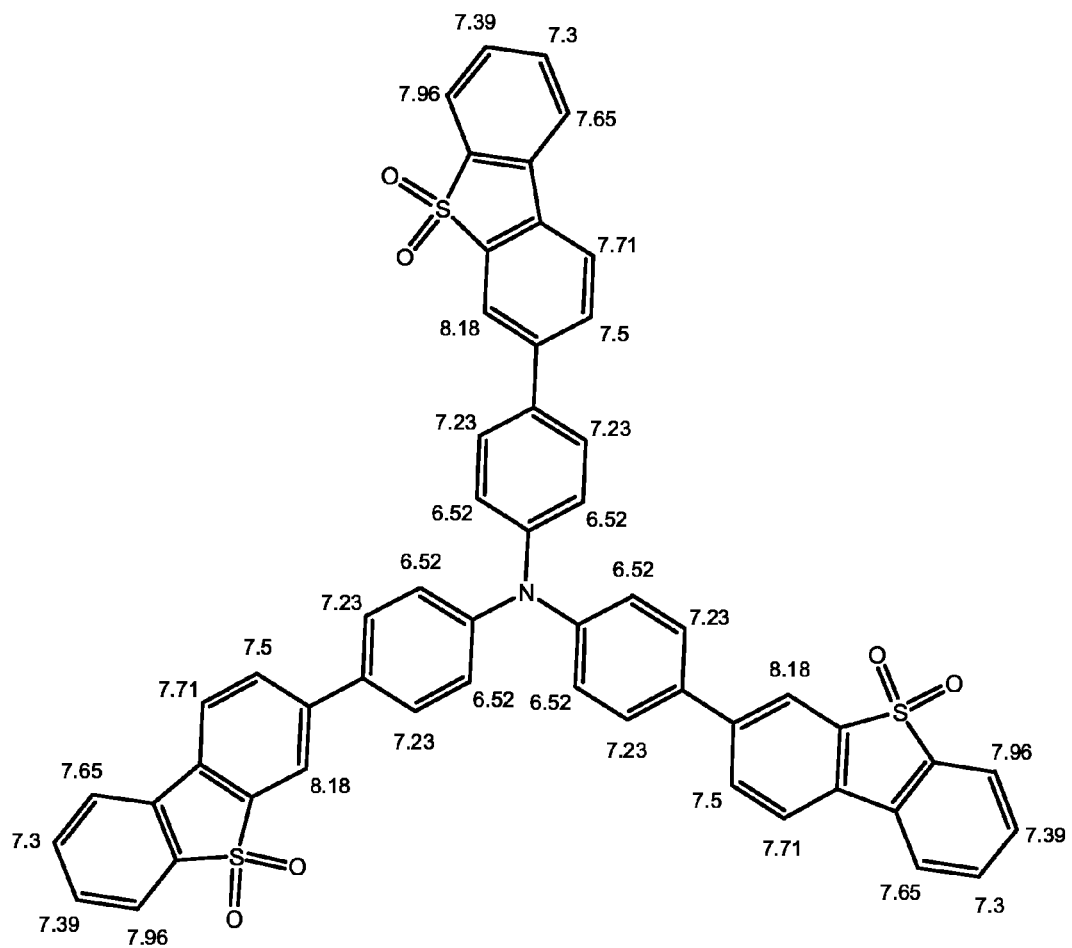
FIG. 1 is a proton (H-1) nuclear magnetic resonance spectrum illustrating a sulfone group-containing compound TFSOTA according to an embodiment of the present invention.
Figure 1:
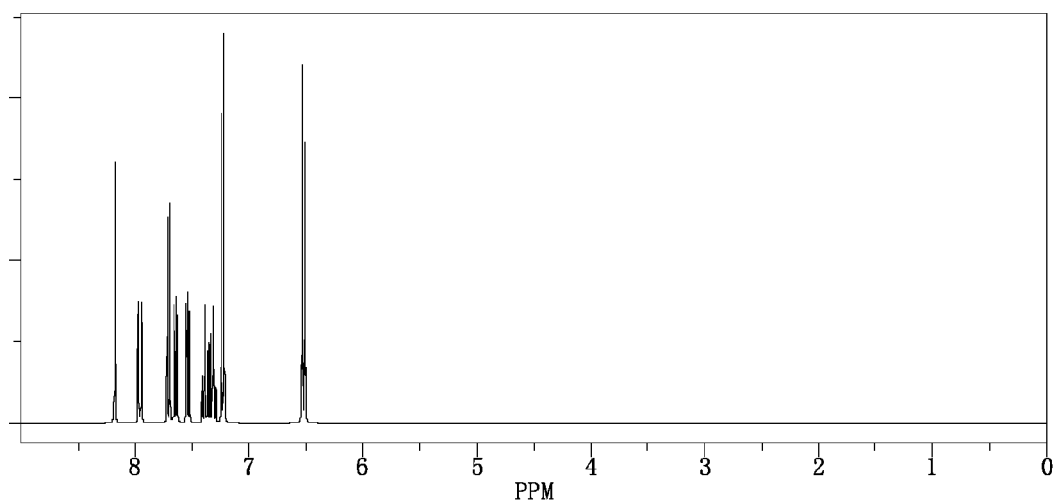

The present invention will now be described more specifically with reference to the following embodiments. It is to be noted that the following descriptions of preferred embodiments of this invention are presented herein for purpose of illustration and description only. It is not intended to be exhaustive or to be limited to the precise form disclosed.

The present invention provides a sulfone group-containing compound having formula as

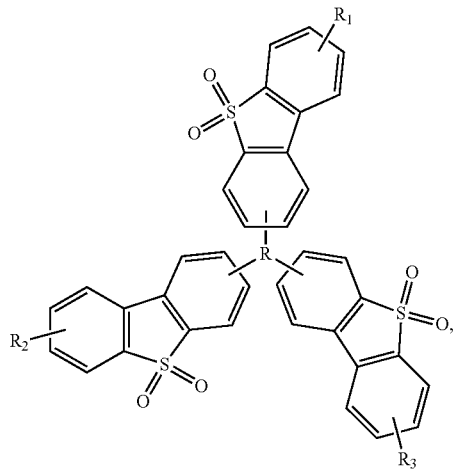

wherein the bridging unit R is capable of connecting to three or more than three fluorene sulfur oxide units; and the unit $R_1$, $R_2$ and $R_3$ respectively connected to the fluorene sulfur oxide units are selected from alkyl chains, aromatic groups or heterocyclic groups. In the formula of the sulfone group-containing compound, the bridging unit R capable of connecting to three or more than three fluorene sulfur oxide units is selected from

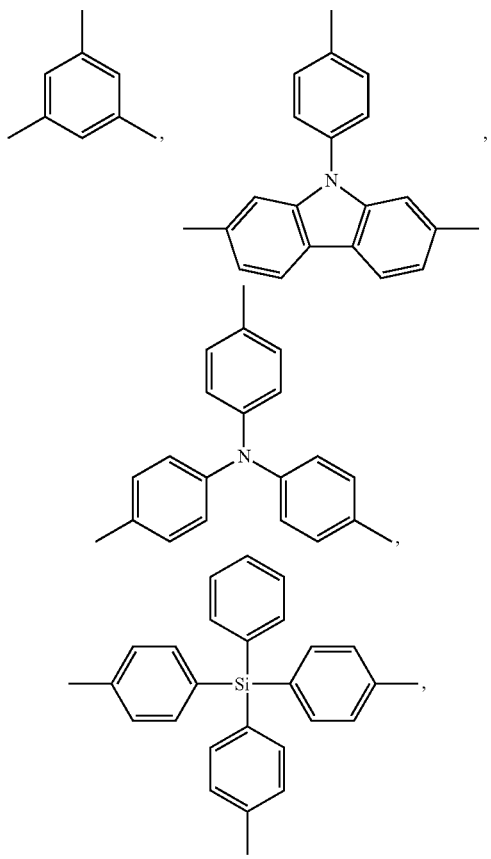

-continued

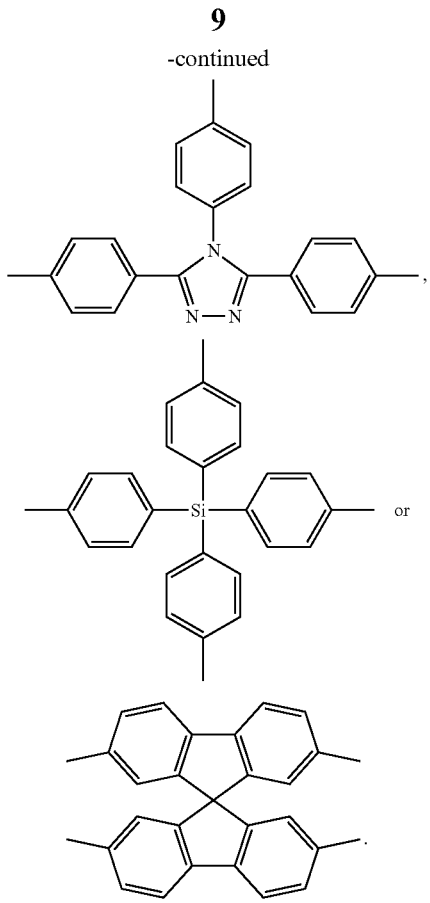

or

In the unit $R_1$, $R_2$ and $R_3$, the alkyl chains are selected from a branched alkyl chain or straight alkyl chains, the branched alkyl chain is such as

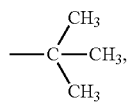

and the straight alkyl chains have formula such as

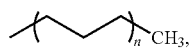

wherein the integer n is in 1-8. In the unit $R_1$, $R_2$ and $R_3$, the aromatic groups are selected from

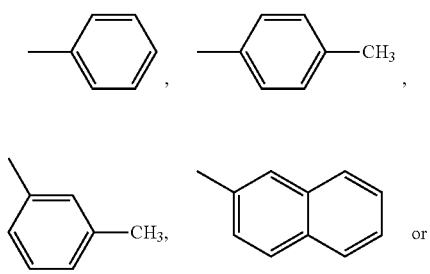

or

-continued

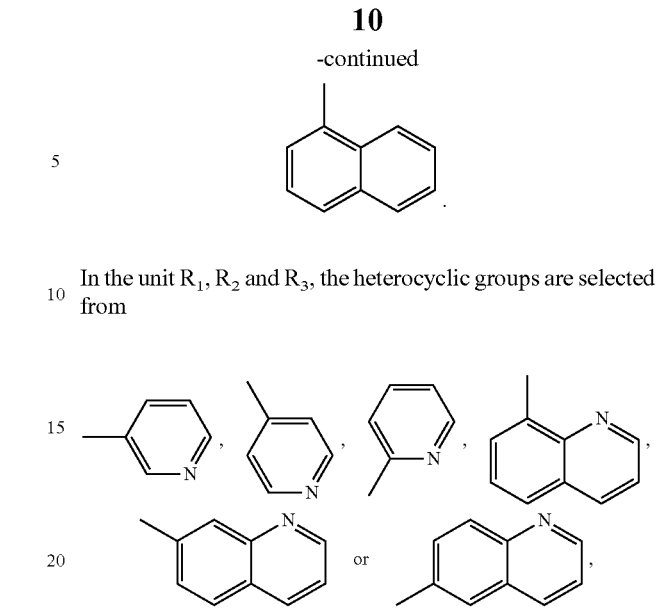

In the unit $R_1$, $R_2$ and $R_3$, the heterocyclic groups are selected from or The unit $R_1$, $R_2$ and $R_3$ include but not limited to the above alkyl chains, aromatic groups or heterocyclic groups, for example, the unit $R_1$, $R_2$ and $R_3$ also can be selected from CN or —$OCH_3$.

According to the present invention, the sulfone group-containing compound has the sulfone group and a star-shaped molecular structure. Because the sulfone group is an electron-withdrawing group, the sulfone group-containing compound have high electron affinity and excellent electron-transporting property. Applying the sulfone group-containing compound to a light emitting layer or an electron transport layer in an OLED device can enhance efficiency of the OLED device. Due to the star-shaped molecule structure, the sulfone group-containing compound has characteristics such as great molecular weight, large steric, high glass-transition temperature, poor crystallinity and easily forming a stable amorphous film, so that lifetime of the OLED device can also be enhanced.

Moreover, in case that the bridging unit R, such as

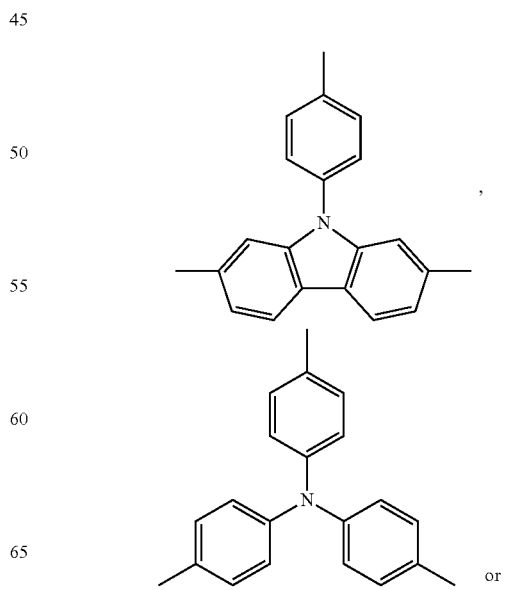

or

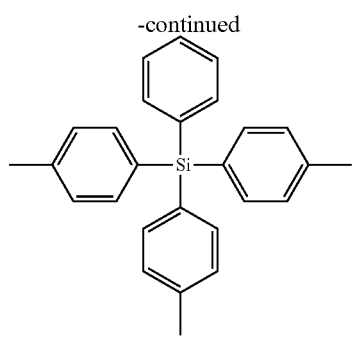

has stronger hole-transporting ability, the sulfone group-containing compound is a dipole material, and applying the sulfone group-containing compound to the light emitting layer in the OLED device can provide a equilibrium between a hole-concentration current and an electron-concentration current so as to expand combination zone of holes and electrons in the entire light emitting layer therein, therefore, efficiency and lifetime of the OLED device can be enhanced. In case that the bridging unit R, such as has stronger electron-transporting ability, the sulfone group-containing compound is an excellent electron-transporting material, and applying the sulfone group-containing compound to the electron transport layer in the OLED device can provide a equilibrium between a hole-concentration current and an electron-concentration current in the light emitting layer, therefore, efficiency and lifetime of the OLED device can be enhanced. Moreover, the sulfone group-containing compound according to the present invention can be applied to an organic photovoltaic (OPV) and an organic thin film transistor (OTFT).

A method of synthesizing the sulfone group-containing compound according to the present invention includes steps as follows. Firstly, 2-bromo fluorene sulfur oxide unit or 3-bromo-fluorene sulfur oxide unit and bridging unit are synthesized. Then, fluorene sulfur oxide unit is reacted with, and connected to the bridging unit. Then, hydrogen atoms connected to the benzene ring of the fluorene sulfur oxide unit are substituted with the unit $R_1$, $R_2$ and $R_3$, and then the sulfone group-containing compound is formed.

The present invention will now be described more specifically with reference to the following embodiments. It is not intended to be exhaustive or to be limited to the precise form disclosed. As the unit $R_1$, $R_2$ and $R_3$ represented as above plural groups are formed with conventional methods, they are not described one by one herein.

Embodiment 1: a reaction equation of synthesizing 4,4',4"-tri(fluorene sulfur oxide-3-yl)triphenylamine (TFSOTA) is represented as:

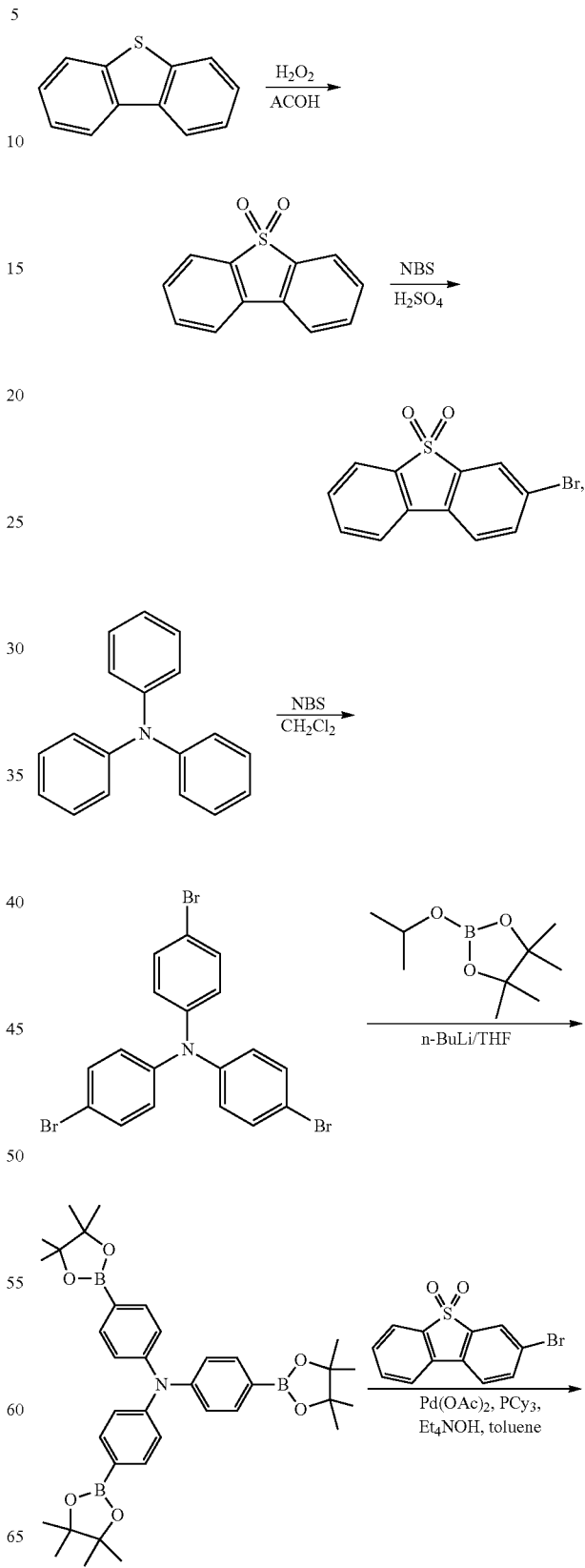

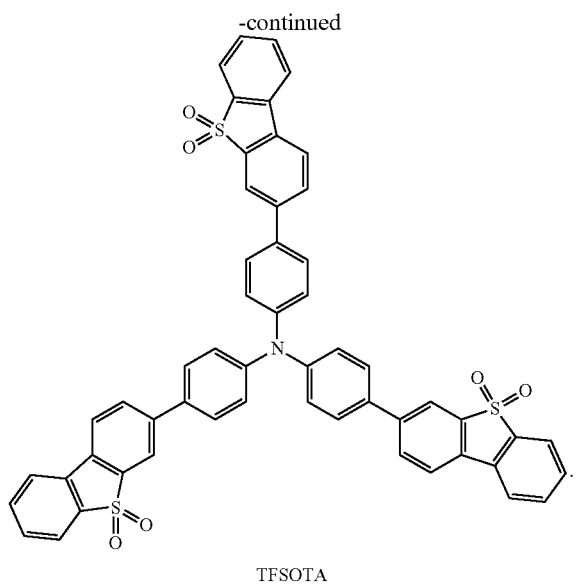

TFSOTA

Synthesizing the fluorene sulfur oxide includes steps as follows. Firstly, 10 g of dibenzothiophene and 80 ml of glacial acetic acid are weighed and added into a 150 ml single-mouth bottle. The dibenzothiophene and glacial acetic acid are heated to reflux by magnetic stirring, then heated to 80° C. After the dibenzothiophene has been completely dissolved, 10 ml of hydrogen peroxide is once added into the 150 ml single-mouth bottle, and the above reactants are gradually warmed up to 110° C. After reaction of the above reactants has been performed for 4 hours, the reaction is stopped, and the above reactants are cooled down to room temperature. A small amount of water is added into the 150 ml single-mouth bottle, and then a solid product formed with the above reactants is filtered, washed three times with water, and washed twice with ethanol to obtain 10 g of white solid by 85% yield.

Synthesizing 3-bromo fluorene sulfur oxide includes steps as follows. Firstly, 10 g of fluorene sulfur oxide is added into a 500 ml three-necked bottle, 150 ml of concentrated sulfuric acid is then added into the 500 ml three-necked bottle, the fluorene sulfur oxide is dissolved by magnetic stirring, and then the concentrated sulfur acid with the dissolved fluorene sulfur oxide is cooled down to 0° C. with ice bath. Then, 8 g of NBS is added portionwise into the 500 ml three-necked bottle. After reaction of the NBS and the concentrated sulfur acid with the dissolved fluorene sulfur oxide has been performed for 24 hours, the above reactants are gradually dropped into ice water to separate out yellow solid, and the yellow solid is filtered, washed twice with sodium bisulfite, washed twice with distilled water, and then washed twice with ethanol. Then, 9 g of white needle type solid by 53% yield is obtained through recrystallization of the washed yellow solid with chlorobenzene.

Synthesizing tri p-bromo triphenylamine includes steps as follows. Firstly, 20 mmol of triphenylamine, 63 mmol of NBS and 400 ml of dichloromethane are weighed and added into 500 ml bottle. Then, the above reactants are stirred to react under dark circumstance. After reaction of the above reactants has been performed for 12 hours, the above reactants are filtered to obtained a filtered reaction solution, the filtered reaction solution is washed three times with a solution of water and sodium hydrogen sulfite, dried the filtered and washed solution with anhydrous sodium sulfate, solvent in the filtered and washed reaction solution is removed to obtain a raw product by rotary evaporation, the raw product is purified by silica gel column chromatography (an eluent: n-hexane), and 8 g of white crystal is obtained.

Synthesizing tri p-(4,4,5,5-tetramethyl-1,3,2-dioxaborolane-2-yl)phenylamine includes steps as follows. Firstly, 20 mmol of 3 p-bromo triphenylamine is weighed and added into a 250 ml three-necked bottle, 200 ml of dry THF is refined, argon is then filled, and the 250 ml three-necked bottle is sealed with a mixture of rosin and paraffin. The 250 ml three-necked bottle containing the above reactants is placed in a cold well filled with liquid nitrogen, and cooled down to −78° C. below. Then, 52 mL solution of n-butyllithium dissolved in 20 ml of 2.5 M hexane is gradually injected into airway of the 250 ml three-necked bottle by using a syringe. After the above reactants has been stirred for 2 hours at −78° C. below, 16 ml of 2-isopropyl-4,4,5,5-tetramethyl-1,3,2-dioxaborolane is added into the 250 ml three-necked bottle to react with the above reactants for 2 hours at the same −78° C. below, a reaction mixture of all the above reactants is naturally warmed up to room temperature, and continues reaction during 24 hours. The reaction mixture is added into water, hydrochloric acid is added dropwise into the reaction mixture till clarification of the reaction mixture being formed, and a product of the reaction mixture is extracted with diethyl ether. An organic layer of the extracted product is washed with aqueous ammonium chloride solution, and dried with anhydrous $MgSO_4$. After solvent in the above washed and dried product has been evaporated under reduced pressure, a pale yellow solid is obtained, white powder solid is obtained from the pale yellow solid recrystallized with methanol and tetrahydrofuran, the white powder solid is purified by silica gel column chromatography (an eluent: an 1:4 ratio mixture of methanol and tetrahydrofuran), and a product is obtained by 66% yield.

Synthesizing TFSOTA includes steps as follows. Firstly, carefully purified tri p-(4,4,5,5-tetramethyl-1,3,2-dioxaborolane-2-yl)phenylamine, 2 mmol of 3-bromo fluorene sulfur oxide, 5 mg of palladium acetate and 10 mg tricyclohexylphosphine are added into a reaction bottle, 20 ml refined toluene, 4 ml of tetraethyl ammonium hydroxide solution (20% weight) and 4 ml of distilled water are protected under argon, then added into the reaction bottle, then heated up to 80-85° C., and then a reaction of the above reactants are performed for 24 hours. Then, after the reaction has been stopped and cool down, the above reactants are precipitated in methanol added dropwise, filtered, purified with column chromatography, and dried to form a product.

Embodiment 2: a reaction equation of synthesizing 4,4',4",4"'-tetra(fluorene sulfur oxide-2-yl)tetraphenylsilane (TFSOTPSI) is represented as:

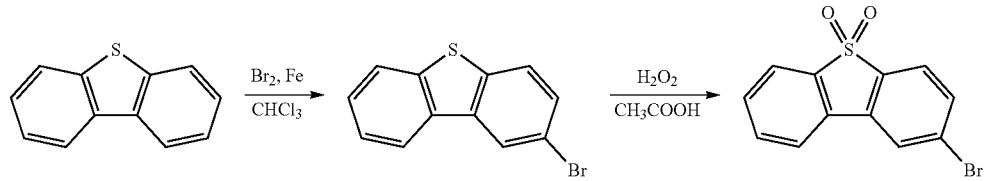

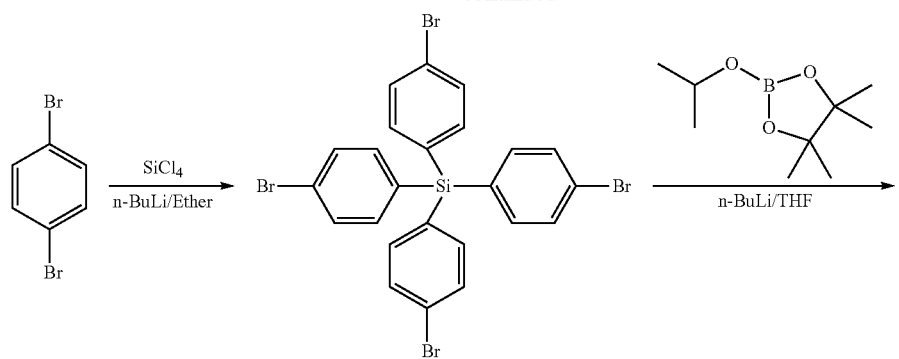
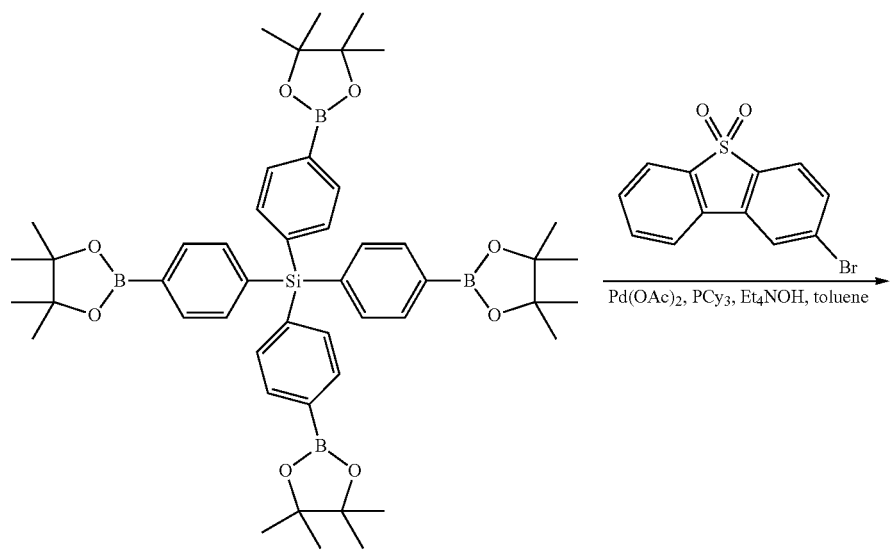
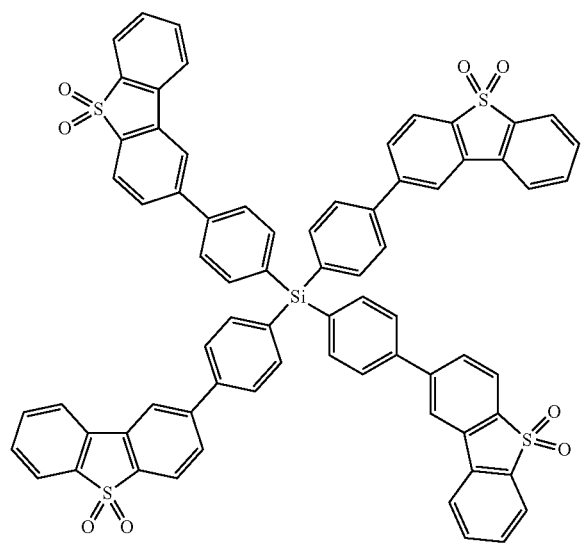
TFSOTPSI

Synthesizing 2-bromo dibenzothiophene includes steps as follows. 20 g of 108.7 mmol dibenzothiophene and 308 mg of 5.5 mmol reduced iron powder are added into a 500 ml single-port flat-bottomed flask, 300 ml $CHCl_3$ is then added into the 500 ml single-port flat-bottomed flask, the dibenzothiophene is dissolved by magnetic stirring, and 20 g of $Br_2$ is gradually dropped into the above reactants with a constant funnel at 0° C. to react for 10 hours under dark circumstance. Then, a saturated solution of sodium hydrogen sulfite is gradually added into the reacted reactants, and the reacted reactants with the saturated solution of sodium hydrogen sulfite are fully stirred and filtered. Then, the filtered reactants is further rinsed with the saturated solution of sodium hydrogen sulfite to obtain a solid, the solid is rinsed with methanol, then dried, and then recrystallized to obtain 22.7 g of a white solid by 66.4% yield.

Synthesizing 2-bromo fluorene sulfur oxide includes steps as follows. Firstly, 10 g of 2-bromo dibenzothiophene and 80 ml of glacial acetic acid are weighed and added into a 150 ml single-mouth bottle. The 2-bromo dibenzothiophene and glacial acetic acid are heated to reflux by magnetic stirring, then heated to 80° C. After the 2-bromo dibenzothiophene has been completely dissolved, 10 ml of hydrogen peroxide is once added into the 150 ml single-mouth bottle, and the above reactants are gradually warmed up to 110° C. After reaction of the above reactants has been performed for 4 hours, the reaction is stopped, and the above reactants are cooled down to room temperature. A small amount of water is added into the 150 ml single-mouth bottle, and then a solid product formed by the above reactants is filtered, washed three times with water, and washed twice with ethanol to obtain 10 g of white solid by 85% yield.

Synthesizing tetra p-bromo phenylsilane includes steps as follows. Firstly, 25 g of 1,4 dibromobenzene is weighed and added into a 500 ml three-necked bottle, 300 ml of dry anhydrous ether is refined, argon is then filled, and the 500 ml three-necked bottle is sealed with a mixture of rosin and paraffin. The 500 ml three-necked bottle containing the above reactants is placed in a cold well filled with liquid nitrogen, and cooled down to −78° C. below. Then, 42.4 ml solution of n-butyllithium dissolved in 20 ml of 2.5 M hexane is gradually injected into airway of the 500 ml three-necked bottle by using a syringe. After the above reactants has been stirred for 2 hours at −78° C. below, a mixture formed with 3 ml of 26.5 mmol silicon tetrachloride in 20 ml of ether is added into the 500 ml three-necked bottle to react with the above reactants for 2 hours at the same −78° C. below, a reaction mixture of all the above reactants is naturally warmed up to room temperature, and continues reaction during 24 hours. The reaction mixture is added into water, hydrochloric acid is added dropwise into the reaction mixture till clarification of the reaction mixture being formed, and a product of the reaction is extracted with diethyl ether. An organic layer of the extracted product is washed with aqueous ammonium chloride solution, and dried with anhydrous $MgSO_4$. After solvent in the above washed and dried product has been evaporated under reduced pressure, a pale yellow solid is obtained, then white powder solid is obtained from the pale yellow solid recrystallized with methanol and tetrahydrofuran, then the white powder solid is purified by silica gel column chromatography, and an eluent is a 1:4 ratio mixture of methanol and tetrahydrofuran.

Synthesizing tetra p-(4,4,5,5-tetramethyl-1,3,2-dioxaborolane-2-yl)phenylamine includes steps as follows. Firstly, 20 mmol of tetra p-bromo triphenylamine is weighed and added into a 250 ml three-necked bottle, 200 ml of dry THF is refined, argon is then filled, and the 250 ml three-necked bottle is sealed with a mixture of rosin and paraffin. The 250 ml three-necked bottle containing the above reactants is placed in a cold well filled with liquid nitrogen, and cooled down to −78° C. below. Then, 52 mL solution of n-butyllithium dissolved in 20 ml of 2.5 M hexane is gradually injected into airway of the 250 ml three-necked bottle by using a syringe. After the above reactants has been stirred for 2 hours at −78° C. below, 16 ml of 2-isopropyl-4,4,5,5-tetramethyl-1,3,2-dioxaborolane is added into the 250 ml three-necked bottle to react with the above reactants for 2 hours at the same −78° C. below, a reaction mixture of all the above reactants is naturally warmed up to room temperature, and continues reaction during 24 hours. The reaction mixture is added into water, hydrochloric acid is added dropwise into the reaction mixture till clarification of the reaction mixture being formed, and a product of the reaction is extracted with diethyl ether. An organic layer of the extracted product is washed with aqueous ammonium chloride solution, and dried with anhydrous $MgSO_4$. After solvent in the above washed and dried product has been evaporated under reduced pressure, a pale yellow solid is obtained, white powder solid is obtained from the pale yellow solid recrystallized with methanol and tetrahydrofuran, then the white powder solid is purified by silica gel column chromatography, and an eluent is a 1:4 ratio mixture of methanol and tetrahydrofuran.

Synthesizing TFSOTPSI includes steps as follows. Firstly, carefully purified tetra p-(4,4,5,5-tetramethyl-1,3,2-dioxaborolane-2-yl)phenylamine, 2 mmol of 2-bromo fluorene sulfur oxide, 5 mg of palladium acetate and 10 mg tricyclohexylphosphine are added into a reaction bottle, 20 ml refined toluene, 4 ml of tetraethyl ammonium hydroxide solution (20% weight) and 4 ml of distilled water are protected under argon, then added into the reaction bottle, then heated up to 80-85° C., and then a reaction of the above reactants are performed for 24 hours. Then, after the reaction has been stopped and cool down, the above reactants are precipitated in methanol added dropwise, filtered, purified with column chromatography, and dried to form a product.

Base on demand, after TFSOTA and TFSOTPSI have been synthesized, the unit R1, R2 and R3 in the sulfone group-containing compound according to the present invention can be formed by substituting hydrogen atoms connected to benzene rings in TFSOTA and TFSOTPSI with conventional methods. When a bridging unit R in the sulfone group-containing compound is different from the compounds selected in the above embodiments, a synthesizing method of forming the sulfone group-containing compound with the different bridging unit R can be performed according to the synthesizing method as described in above embodiments.

According to the present invention, sulfone groups-containing compound combines not only electron affinity and transport properties of the fluorene sulfur oxide units, but also spatial characteristics of the star-shaped molecular structure, and the bridging unit R formed therein further provides hole-transporting or electron-transporting abilities. Both TFSOTA and 3,4,5-tri(fluorine sulfur oxide-3-yl)-1,2,4-triazole (TFSOTAZ) are the sulfone group-containing compound, and exemplarily used for describing properties of the sulfone group-containing compounds. TFSOTAZ has a formula as

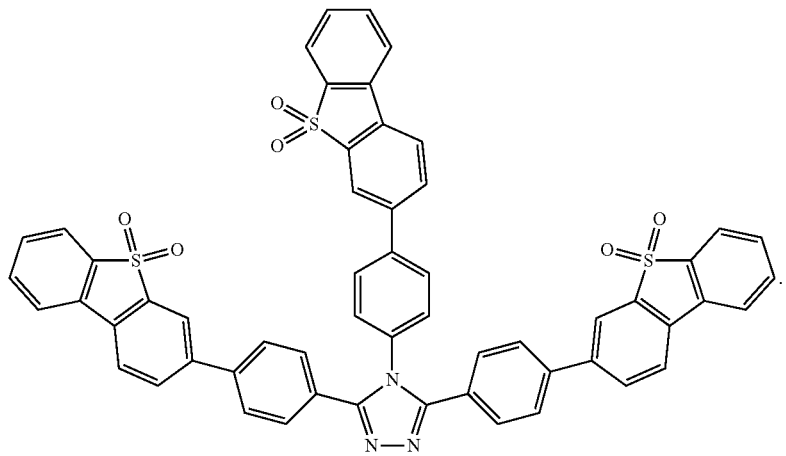 [SMILES: O=S1(=O)c2ccccc2-c2ccc(-c3ccc(-c4nnc(-c5ccc(-c6ccc7c(c6)S(=O)(=O)c6ccccc6-7)cc5)n4-c4ccc(-c5ccc6c(c5)S(=O)(=O)c5ccccc5-6)cc4)cc3)cc21]

Figure 2:
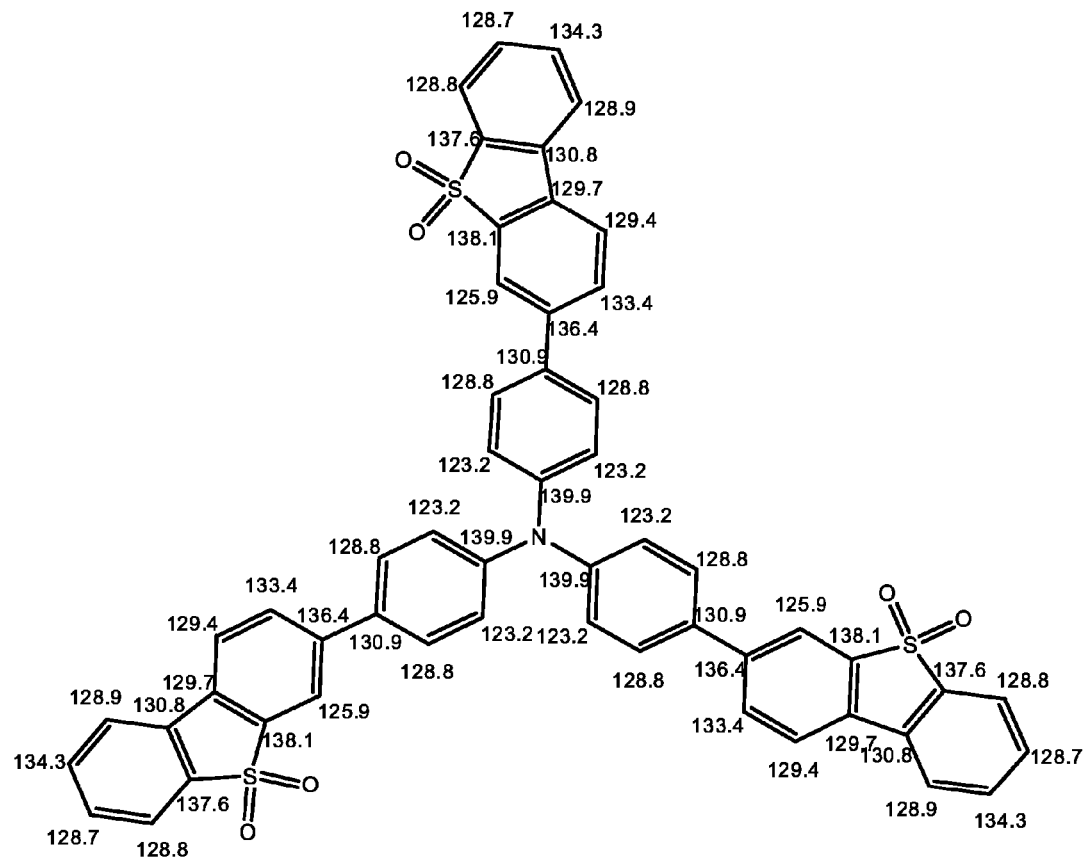
FIG. 2 is a carbon 13 (C-13) nuclear magnetic resonance spectrum illustrating a sulfone group-containing compound TFSOTA according to an embodiment of the present invention.
Figure 2:
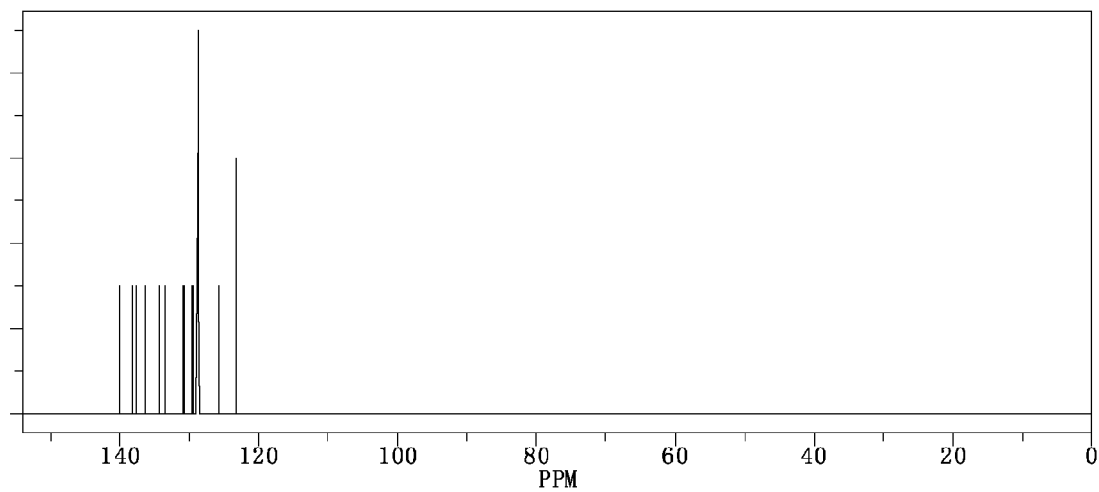

FIG. 1 is a proton (H-1) nuclear magnetic resonance (NMR) spectrum illustrating a sulfone group-containing compound TFSOTA according to an embodiment of the present invention. Please refer to FIG. 1, the proton (H-1) NMR data of TFSOTA is based on a simulation result of Chemdraw2004 software. FIG. 2 is a carbon 13 (C-13) nuclear magnetic resonance spectrum illustrating a sulfone group-containing compound TFSOTA according to an embodiment of the present invention. Please refer to FIG. 2, and the carbon 13 (C-13) NMR data of TFSOTA is based on a simulation result of Chemdraw2004 software.

Figure 3:
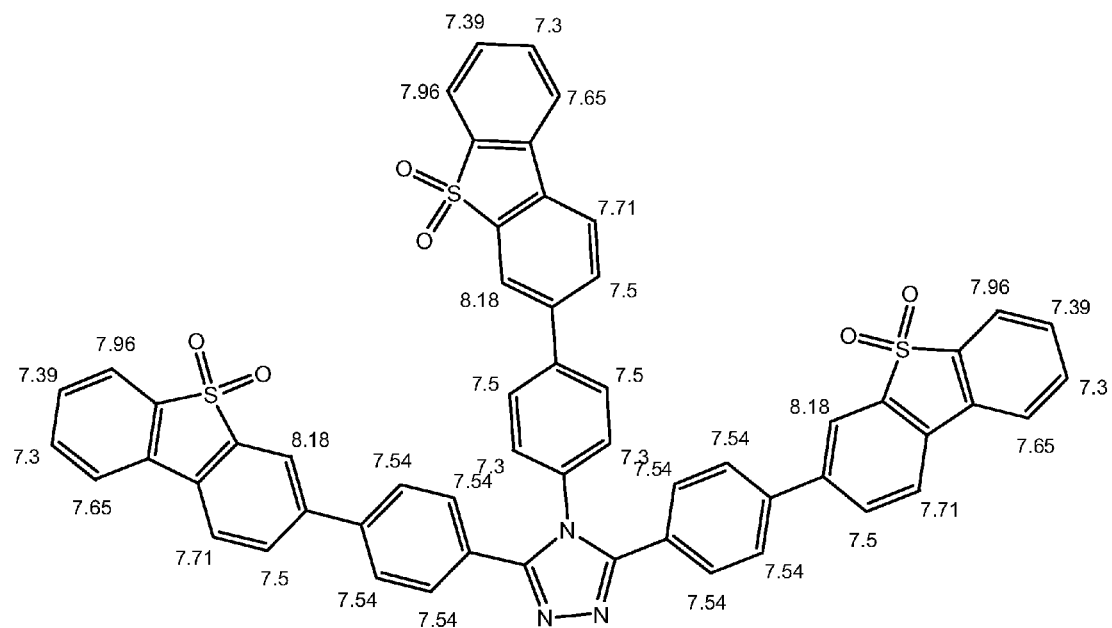
FIG. 3 is a proton (H-1) nuclear magnetic resonance spectrum illustrating a sulfone group-containing compound TFSOTAZ according to an embodiment of the present invention.
Figure 3:
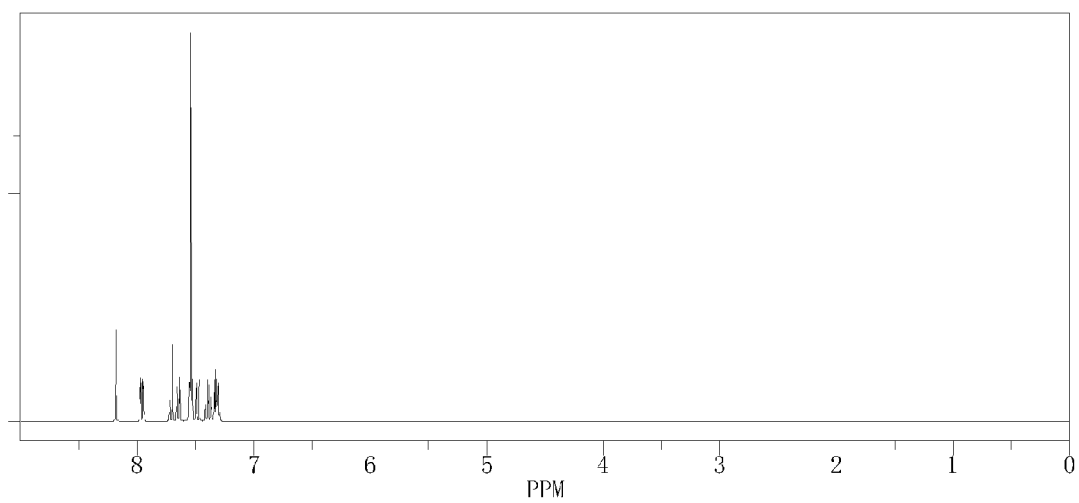
Figure 4:
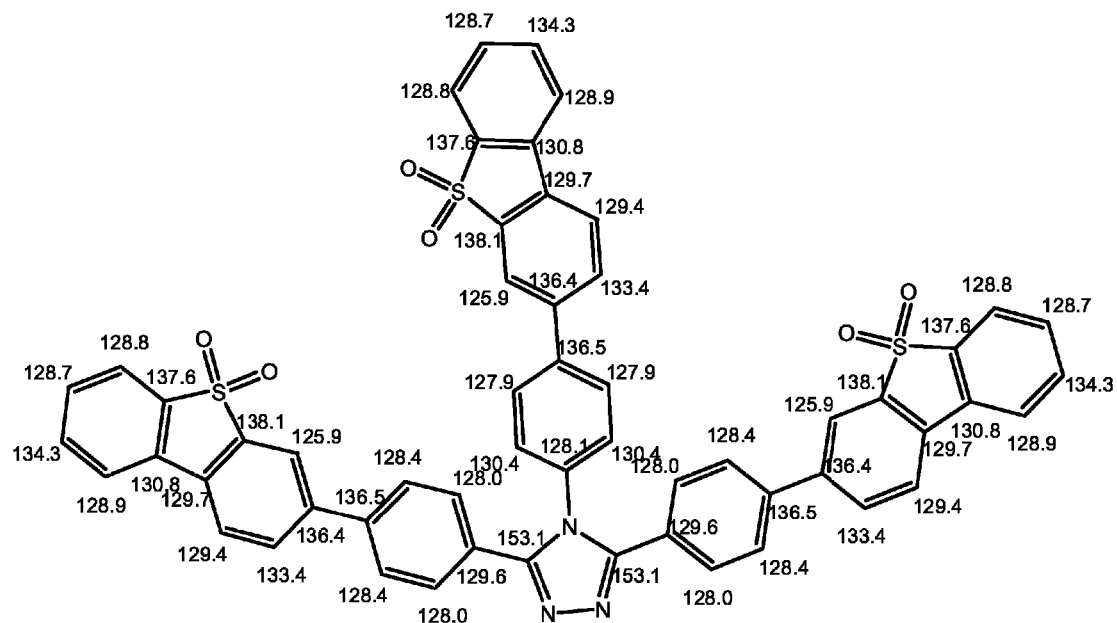
FIG. 4 is a carbon 13 (C-13) nuclear magnetic resonance spectrum illustrating a sulfone group-containing compound TFSOTAZ according to an embodiment of the present invention.
Figure 4:
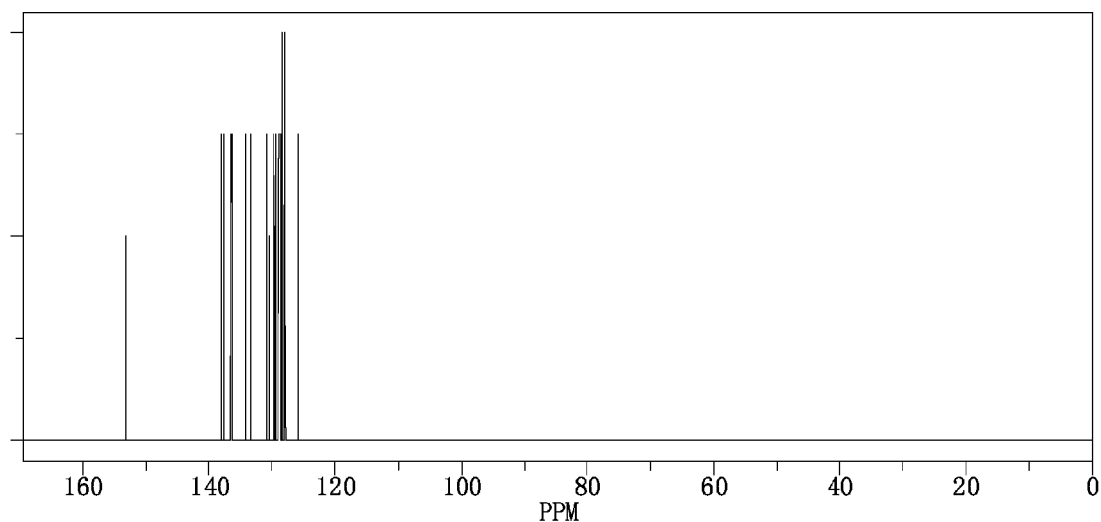

FIG. 3 is a proton (H-1) nuclear magnetic resonance (NMR) spectrum illustrating a sulfone group-containing compound TFSOTAZ according to an embodiment of the present invention. Please refer to FIG. 3, the proton (H-1) NMR data of TFSOTA is based on a simulation result of Chemdraw2004 software. FIG. 4 is a carbon 13 (C-13) nuclear magnetic resonance spectrum illustrating a sulfone group-containing compound TFSOTAZ according to an embodiment of the present invention. Please refer to FIG. 4, and the carbon 13 (C-13) NMR data of TFSOTA is based on a simulation result of Chemdraw2004 software.

It is clear that both sulfone group-containing compounds TFSOTA and TFSOTAZ have fluorene sulfur oxide groups, wherein the sulfone group formed in the fluorene sulfur oxide group is the electron-withdrawing group, and has higher electron affinity and an energy band gap of approximately 2.8 eV; therefore, the fluorene sulfur oxide can easily conduct electrons for injection and transport. S atom in the sulfone group is at the highest valence state, so as the sulfone group can be a stronger antioxidant, thus the fluorene sulfur oxide has a strong thermal stability. Due to the sulfone group-containing compounds TFSOTA and TFSOTAZ according to the present invention having star-shaped molecule structure and great molecular weight, both glass transition temperatures thereof can be expected are high, and the high glass transition temperatures lead to poor crystallinity and easily forming a stable amorphous film. Therefore, efficiency and lifetime of the OLED device can be enhanced with the sulfone group-containing compound such as TFSOTA and TFSOTAZ.

A bridging unit R in TFSOTAZ is

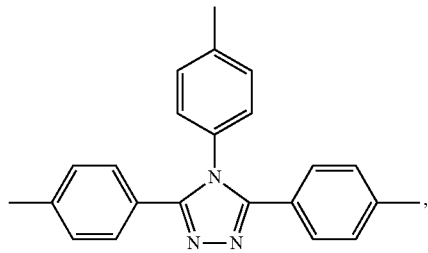

and has stronger electron-transporting ability, so that TFSO-TAZ is an excellent electron-transporting material and preferred to be used in electron transport layer to enhance electron mobility and electron-concentration current in the OLED device, so as to allow equilibrium formed between hole-concentration and electron-concentration current and to enhance efficiency of the OLED device.

A bridging unit R in TFSOTA is

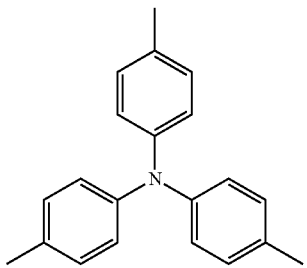

and has stronger hole-transporting ability, TFSOTAZ is a dipole material and preferred to be used as a body material of electroluminescence (EL) to enhance electron mobility and electron-concentration current in the OLED device, so as to allow equilibrium between hole-concentration and electron-concentration current, to enlarge entire combination zone, and to enhance lifetime of the OLED device.

Figure 5:
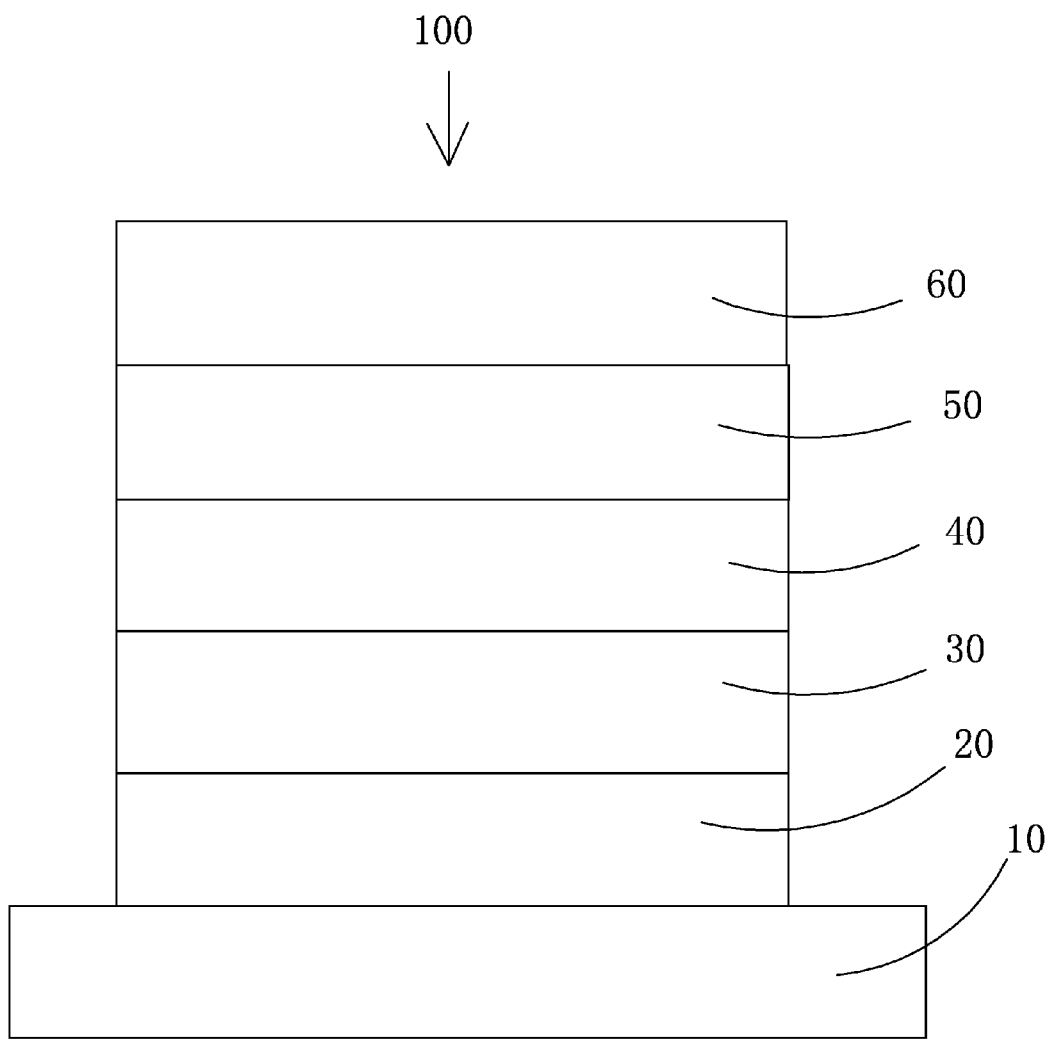
FIG. 5 is schematic cross-sectional views illustrating an OLED device using a sulfone group-containing compound according to an embodiment of the present invention.

FIG. 5 is schematic cross-sectional views illustrating an OLED device using a sulfone group-containing compound according to an embodiment of the present invention. As shown in FIG. 5, the OLED device 100 includes a transparent substrate 10, an anode 20, a hole transport layer 30, a light emitting layer 40, an electron transport layer 50 and a cathode 60. The anode 20 is disposed above the transparent substrate 10. The hole transport layer 30 is disposed above the anode 20. The light emitting layer 40 is disposed above the hole transport layer 30. The electron transport layer 50 is disposed above the light emitting layer 40. The cathode 60 is disposed above the electron transport layer 50, wherein at least the electron transport layer 50 or the light emitting layer 40 includes a sulfone group-containing compound. In this embodiment, one or more than one hole transport layer; one or more than one light emitting layer above the hole transport layer; one or more than one electron transport layer can be selectively formed in the OLED device.

The sulfone group-containing compound formed in the light emitting layer 40 or the electron transport layer 50 can be fabricated as following proposal.

In case the light emitting layer 40 includes the sulfone group-containing compound, the sulfone group-containing compound is a single body material of the light emitting layer or mixed with other body materials (i.e. as one of plural components contained in the light emitting layer), whereas the sulfone group-containing compound is as one of plural components contained in the light emitting layer, a weight ratio of the sulfone group-containing compound to the light emitting layer is in 1%~99%, wherein a preferred weight ratio thereof is 5%~95%.

In case the electron transport layer 50 includes the sulfone group-containing compound, the electron transport layer 50 can be a single layer. For the sake of competing energy level of the light emitting layer 40, a number of the electron transport layer 50 can be two or more than two layers, and any electron transport layer 50 can includes the sulfone group-containing compound. The sulfone group-containing compound can be a single body material of the electron transport layer or mixed with other body materials (i.e. one component of plural body materials contained in the electron transport layer), whereas the sulfone group-containing compound is one component of plural body materials contained in the electron transport layer, a weight ratio of the sulfone group-containing compound to the electron transport layer is in 1%~99%, wherein a preferred weight ratio thereof is 5%~95%. Due to the sulfone group-containing compound includes the electron-withdrawing group (i.e. sulfone group), so that the sulfone group-containing compound has higher electron affinity and electron-transporting ability, and the sulfone group-containing compound used as an electron-transporting material can contribute electron injection and transport.

In this preferred embodiment, the sulfone group-containing compound has a formula as

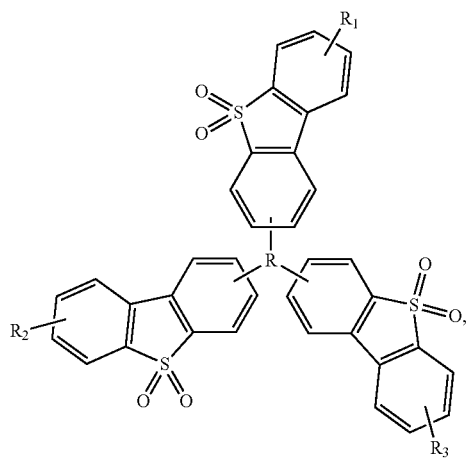

wherein the bridging unit R is capable of connecting to three or more than three fluorene sulfur oxide units; and the unit $R_1$, $R_2$ and $R_3$ respectively connected to the fluorene sulfur oxide units are selected from alkyl chains, aromatic groups or heterocyclic groups.

In this preferred embodiment, the bridging unit R capable of connecting to three or more than three fluorene sulfur oxide units is selected from

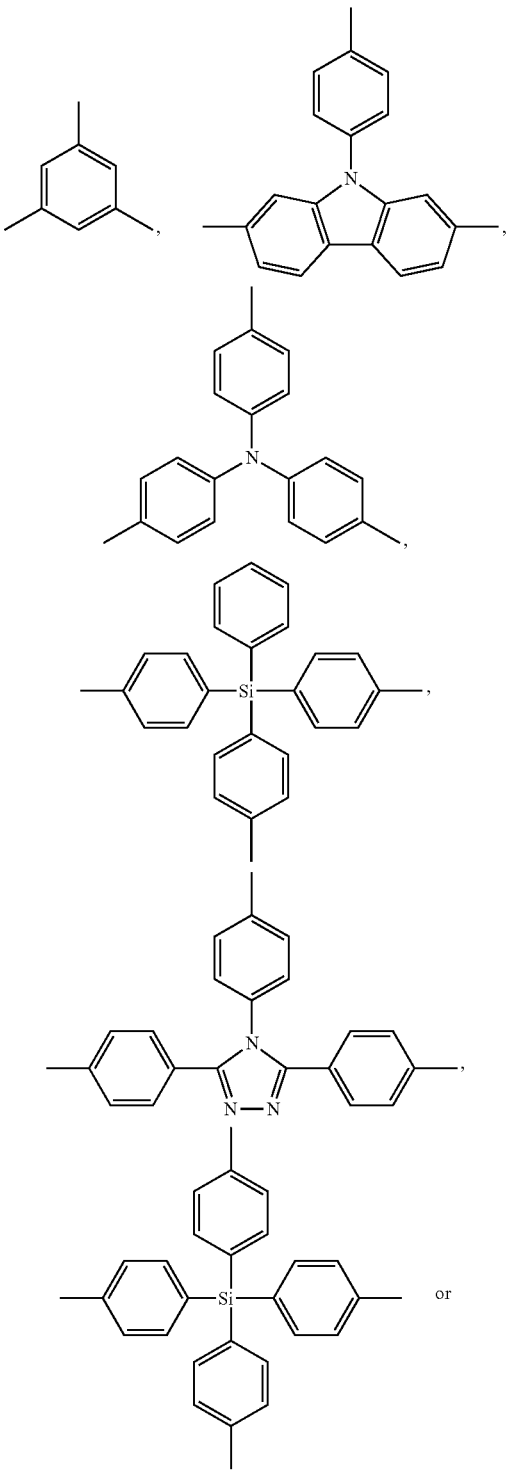

or

-continued

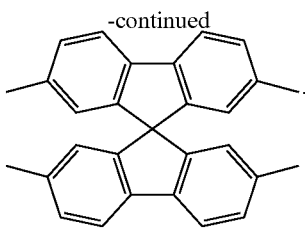

In this preferred embodiment, the alkyl chains can be selected from a branched alkyl chain such as

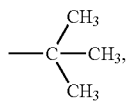

or straight alkyl chains such as

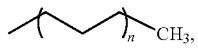

wherein the integer n is in 1-8.

In this preferred embodiment, the aromatic groups can be selected from

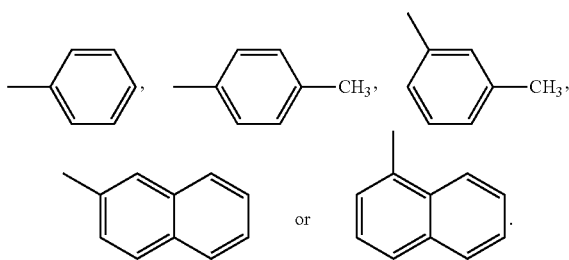

In this preferred embodiment, the heterocyclic groups can be selected from

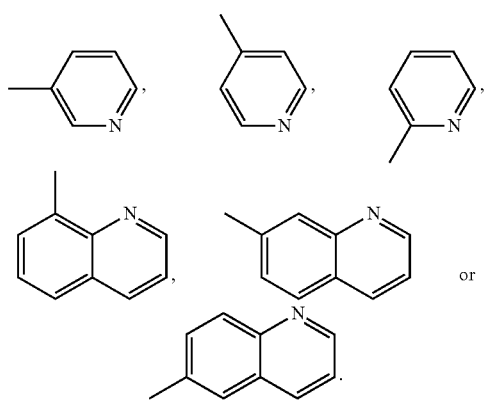

The unit $R_1$, $R_2$ and $R_3$ include but not limited to the above alkyl chains, aromatic groups or heterocyclic groups, for example, the unit $R_1$, $R_2$ and $R_3$ also can be selected from CN or —$OCH_3$.

Due to the sulfone group-containing compound has star-shaped molecule structure, the sulfone group-containing compound contributes electron injection and transport to enhance efficiency of the OLED device 100, additionally, it has characteristics such as great molecular weight, large steric, high glass-transition temperature, poor crystallinity and easily forming a stable amorphous film to enhance lifetime of the OLED device 100.

Moreover, in case that bridging unit R in the sulfone group-containing compound has stronger hole-transporting ability, the strsulfone group-containing compound is a dipole material preferred to be used as a body material of the light emitting layer 40 so as to allow equilibrium between hole-concentration and electron-concentration current, to enlarge entire combination zone, and to enhance lifetime of the OLED device 100. In case that the bridging unit R has stronger electron-transporting ability, the sulfone group-containing compound is an excellent electron-transporting material and preferred to be used in electron transport layer 50 to enhance electron mobility and electron-concentration current in the OLED device 100, so as to allow equilibrium formed between hole-concentration and electron-concentration current in the light emitting layer 40, and to enhance efficiency of the OLED device 100.

Figure 6:
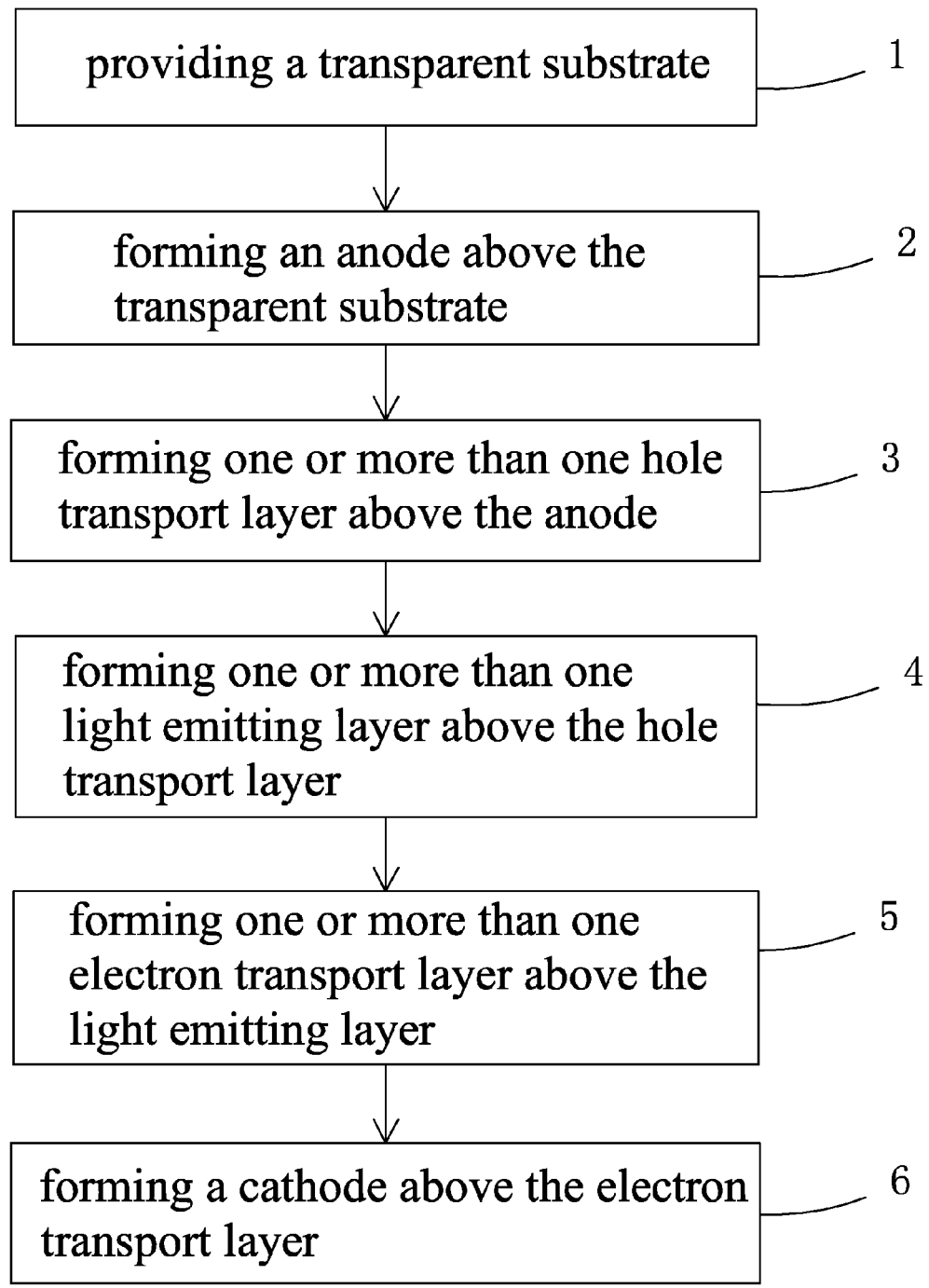
FIG. 6 is schematic cross-sectional views illustrating a partial process flow of a method of fabricating an OLED device using a sulfone group-containing compound according to an embodiment of the present invention.

FIG. 6 is schematic cross-sectional views illustrating a partial process flow of a method of fabricating an OLED device using a sulfone group-containing compound according to an embodiment of the present invention. As shown in FIG. 6, the method includes steps as follows:

Step 1, providing a transparent substrate;
Step 2, forming an anode above the transparent substrate;
Step 3, forming one or more than one hole transport layer above the anode;
Step 4, forming one or more than one light emitting layer above the hole transport layer;
Step 5, forming one or more than one electron transport layer above the light emitting layer; and
Step 6, forming a cathode above the electron transport layer, wherein at least one of the light emitting layer 40 or the electron transport layer 50 includes the sulfone group-containing compound.

In this preferred embodiment, In a preferred embodiment, Step 4 in the method of fabricating the OLED device using the sulfone group-containing compound includes forming the sulfone group-containing compound above the hole transport layer 30 with a vacuum evaporation deposition. The sulfone group-containing compound can be a single body material or mixed with other body materials to form the light emitting layer 40 with the vacuum evaporation deposition. In case that the sulfone group-containing compound is one component of plural body materials contained in the light emitting layer 40, a weight ratio of the sulfone group-containing compound to the light emitting layer is in 1%~99%, wherein a preferred weight ratio thereof is 5%~95%.

In this preferred embodiment, Step 5 includes forming the sulfone group-containing compound above the light emitting layer 40 with a vacuum evaporation deposition. For the sake of competing energy level of the light emitting layer 40, a number of the electron transport layer 50 can be two or more than two layers, and the sulfone group-containing compound can be form any electron transport layer 50 with the vacuum evaporation deposition. The sulfone group-containing compound can be a single body material of the electron transport layer or mixed with other electron-transporting material (i.e. one component of plural body materials in the electron transport layer formed with the vacuum evaporation deposition), whereas the sulfone group-containing compound is one component of plural body materials contained in the electron transport layer, a weight ratio of the sulfone group-containing compound to the electron transport layer is in 1%~99%, wherein a preferred weight ratio thereof is 50%~95%.

In general, the sulfone group-containing compound according to the present invention connects to three or more than three fluorene sulfur oxide units with a bridging unit to form a novel star-shaped molecular structure. The sulfone groups-containing compound combines electron affinity and transport properties of the fluorene sulfur oxide units and spatial characteristics of the star-shaped molecular structure, so that efficiency and lifetime of an OLED device using the same can be enhanced While the invention has been described in terms of what is presently considered to be the most practical and preferred embodiments, it is to be understood that the invention needs not be limited to the disclosed embodiment. On the contrary, it is intended to cover various modifications and similar arrangements included within the spirit and scope of the appended claims which are to be accorded with the broadest interpretation so as to encompass all such modifications and similar structures.

What is claimed is:

1. A sulfone group-containing compound having three or four fluorene sulfur oxide groups, wherein a formula of the sulfone group-containing compound having three fluorene sulfur oxide groups is as:

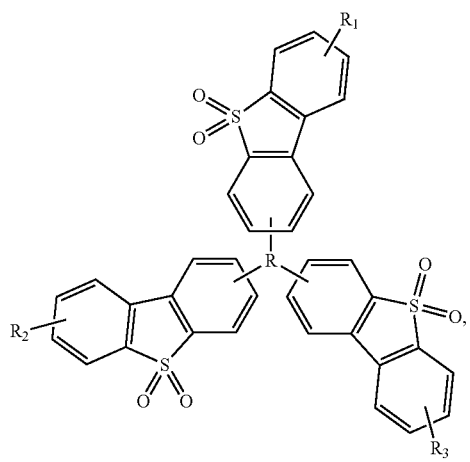

wherein the bridging unit R is selected from

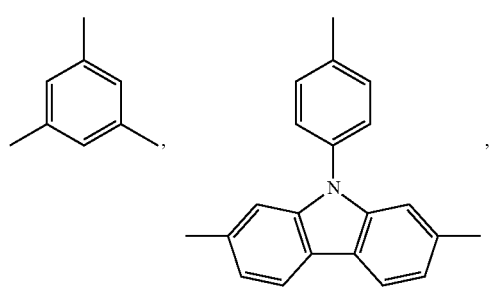

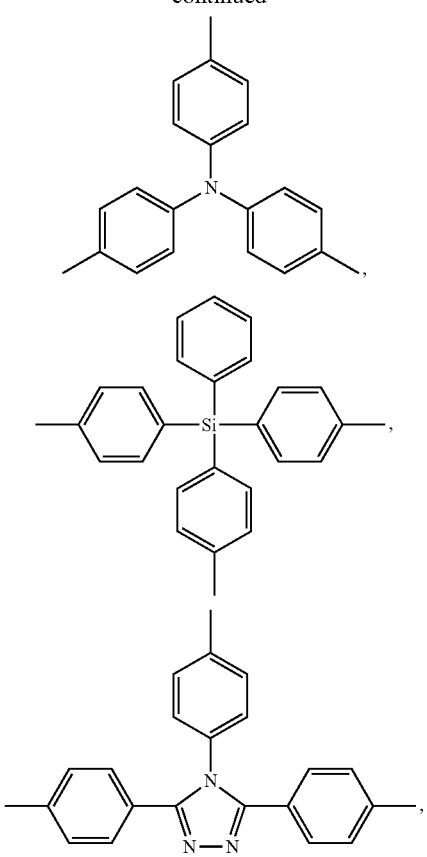

and the groups R1, R2 and R3 respectively connected to the fluorene sulfur oxide groups are selected from alkyl chains, aromatic groups or heterocyclic groups; and a formula of the sulfone group-containing compound having four fluorene sulfur oxide groups is as

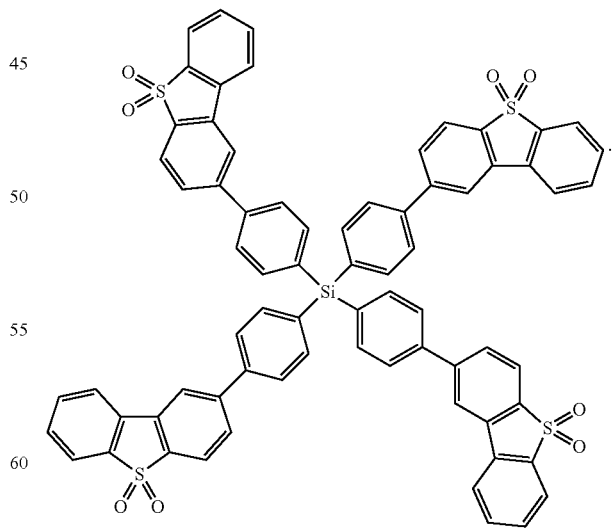

2. The sulfone group-containing compound according to claim 1, wherein the alkyl chains are selected from a branched alkyl chain or straight alkyl chains.

3. The sulfone group-containing compound according to claim 2, wherein the branched alkyl chain is

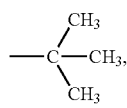

and the straight alkyl chains have formula as

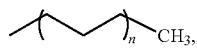

wherein the integer n is 1-8.

4. The sulfone group-containing compound according to claim 1, wherein the aromatic groups are selected from

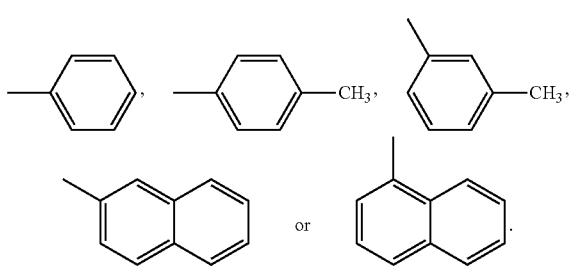

5. The sulfone group-containing compound according to claim 1, wherein the heterocyclic groups are selected from

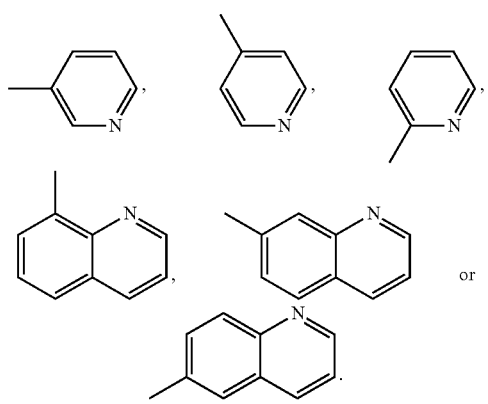

6. An organic light emitting diode (OLED) device having a sulfone group-containing compound, comprising:
   a transparent substrate;
   an anode, disposed above the transparent substrate;
   a hole transport layer, disposed above the anode;
   a light emitting layer, disposed above the hole transport layer;
   an electron transport layer, disposed above the light emitting layer; and
   a cathode, disposed above the electron transport layer, wherein at least the electron transport layer or the light emitting layer comprises a sulfone group-containing compound having three or four fluorene sulfur oxide groups, wherein a formula of the sulfone group-containing compound having three fluorene sulfur oxide groups is as

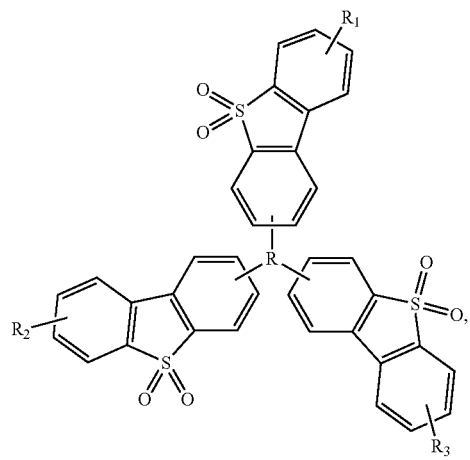

wherein the bridging unit R is selected from

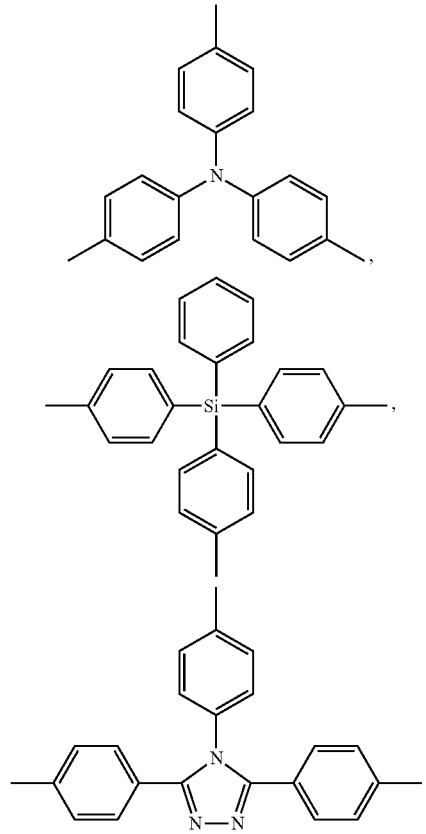

and the groups R1, R2 and R3 respectively connected to the fluorene sulfur oxide groups are selected from alkyl chains, aromatic groups or heterocyclic groups; and a formula of the sulfone group-containing compound having four fluorene sulfur oxide groups is as

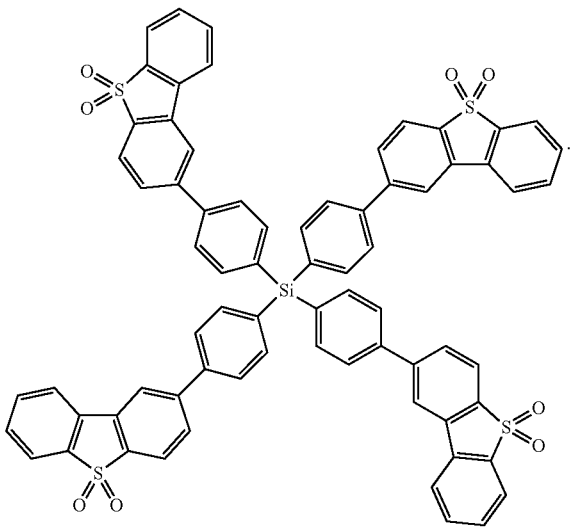 [SMILES: O=S1(=O)c2ccccc2-c2cc(-c3ccc([Si](c4ccc(-c5ccc6c(c5)-c5ccccc5S6(=O)=O)cc4)(c4ccc(-c5ccc6c(c5)-c5ccccc5S6(=O)=O)cc4)c4ccc(-c5ccc6c(c5)-c5ccccc5S6(=O)=O)cc4)cc3)ccc21]

7. The OLED device according to claim 6, when the light emitting layer comprises the sulfone group-containing compound, the sulfone group-containing compound is used as single host material of the light emitting layer or a component of host materials of the light emitting layer, whereas the sulfone group-containing compound is used as the component of host materials of the light emitting layer, a weight ratio of the sulfone group-containing compound to the light emitting layer is 1%~99%; when the electron transport layer comprises the sulfone group-containing compound, the sulfone group-containing compound is used as single material of the electron transport layer or a component of materials of the electron transport layer, whereas the sulfone group-containing compound is used as the component of materials of the electron transport layer, a weight ratio of the sulfone group-containing compound to the electron transport layer is 1%~99%.

8. A method of fabricating the OLED device according to claim 6, comprising steps as follows:
   Step 1, providing a transparent substrate;
   Step 2, forming an anode above the transparent substrate;
   Step 3, forming one or more than one hole transport layer;
   Step 4, forming one or more than one light emitting layer above the hole transport layer;
   Step 5, forming one or more than one electron transport layer above the light emitting layer; and
   Step 6, forming a cathode above the electron transport layer, wherein at least one of the light emitting layer or the electron transport layer comprises the sulfone group-containing compound according to claim 7.

9. The method of fabricating the OLED device according to claim 8, wherein Step 4 comprises forming the sulfone group-containing compound above the hole transport layer with a vacuum evaporation deposition, the sulfone group-containing compound is used as single host material of the light emitting layer or a component of host materials of the light emitting layer, whereas the sulfone group-containing compound is used as the component of host materials of the light emitting layer, a weight ratio of the sulfone group-containing compound to the light emitting layer is 1%~99%.

10. The method of fabricating the OLED device according to claim 8, wherein Step 5 comprises forming the sulfone group-containing compound above the light emitting layer with a vacuum evaporation deposition, and the sulfone group-containing compound is used as single material of the electron transport layer or a component of materials of the electron transport layer, whereas the sulfone group-containing compound is used as the component of materials of the electron transport layer, a weight ratio of the sulfone group-containing compound to the electron transport layer is 1%~99%.

* * * * *